(12) United States Patent
Figdor et al.

(10) Patent No.: US 7,691,591 B2
(45) Date of Patent: Apr. 6, 2010

(54) METHODS OF IDENTIFYING AND ISOLATING CELLS EXPRESSING DC-SIGN

(75) Inventors: Carl Gustav Figdor, Den Bosch (NL); Ruurd Torensma, Nijmegen (NL); Petrus Leonardus Everardus Maria Van Lent, Nijmegen (NL); Wim B. Van Den Berg, Molenhoek (NL)

(73) Assignee: Stichting Katholieke Universiteit, Nijmegen (NL)

( * ) Notice: Subject to any disclaimer, the term of this patent is extended or adjusted under 35 U.S.C. 154(b) by 1149 days.

(21) Appl. No.: 10/524,394

(22) PCT Filed: Sep. 19, 2003

(86) PCT No.: PCT/IB03/05181

§ 371 (c)(1),
(2), (4) Date: Dec. 12, 2005

(87) PCT Pub. No.: WO2004/026909

PCT Pub. Date: Apr. 1, 2004

(65) Prior Publication Data

US 2006/0121033 A1  Jun. 8, 2006

Related U.S. Application Data

(60) Provisional application No. 60/412,624, filed on Sep. 20, 2002.

(51) Int. Cl.
G01N 35/567 (2006.01)
G01N 33/563 (2006.01)
G01N 33/53 (2006.01)
(52) U.S. Cl. .................. 435/7.21; 435/7.1; 435/7.2
(58) Field of Classification Search .............. None
See application file for complete search history.

(56) References Cited

U.S. PATENT DOCUMENTS

| 6,605,279 | B2 | 8/2003 | Freeman et al. | |
|---|---|---|---|---|
| 7,148,329 | B1 * | 12/2006 | Figdor et al. | 530/387.1 |
| 2003/0232745 | A1 | 12/2003 | Olson et al. | |

FOREIGN PATENT DOCUMENTS

| WO | WO 93/01820 | 2/1993 |
|---|---|---|
| WO | WO 95/32734 | 12/1995 |
| WO | WO 96/23882 | 8/1996 |
| WO | WO 98/02456 | 1/1998 |
| WO | WO-9828332 | 7/1998 |
| WO | WO 98/41633 | 9/1998 |
| WO | WO 98/49306 | 11/1998 |
| WO | WO-9855508 | 12/1998 |
| WO | WO 00/63251 | 10/2000 |

OTHER PUBLICATIONS

Soilleux et al., Constitutive and induced expression of DC-SIGN on dendritic cell and macrophage subpopulations in situ and in vitro. Journal of Leukocyte Biology 71:445-457, 2002.*
Mummid et al., Extensive repertoire of membrane-bound and soluble dendritic cell-specific ICAM-3-grabbing nonintegrin 1 (DC-SIGN1) and DC-SIGN2 isoforms, J. Biol. Chem. 276(35):33196-33212 (2001).
Amersdorfer et al., *Infection and Immunity*, 65, pp. 3743-3752 (1997).
Andre et al., *Journal of Virology*, 72(2), pp. 1497-1503(1998).
Baribaud, Frederic, et al., "Functional and Antigenic Characterization of Human, Rhesus Macaque, Pigtailed Macaque, and Murine DC-SIGN," *Journal of Virology*, 75(21), pp. 10281-10289 (2001).
Berkower, I., et al., "Chimeric HIV-1 Envelope GP120-Hepatitis B Core Antigen (HbcAg) Fusion Proteins for HIV-1 Vaccines," FASEB Journal, 10(6):A1082 (1996).
Biosis Database, PREV 197866028654 & Kataoka et al., *Cancer Research*, 38(5), pp. 1202-1207 (1987).
Cohen, *Science*, 287, p. 1567 (2000).
Curtis, BM, et al., "Sequence and Expression of a Membrane-Associated C-type Lectin that Exhibits CD4-Independent Binding of Human Immunodeficiency Virus Envelope Glycoprotein GP 120," Proc. Natl. Acad. Sci. USA 89:8356-8360 (1992).
Eck J., et al., "Cloning of the Mistletoe Lectin Gene and Characterization of the Recombinant A-Chain," European Journal of Biochemistry, 264:775-784 (1999).
Engering, Anneke, et al., "The Dendritic Cell-Specific Adhesion Receptor DC-SIGN Internalizes Antigen for Presentation to T Cells," *J. of Immun.*, 168, pp. 2118-2126 (2000).
FDA Approves Second Indication for Monolclonal Antibody, Jun. 28, 1993, printed on Nov. 12, 2004 from http://www.fda.gov/bbs/topics/ANSWERS/ANS00506.html, Jun. 28, 1993.
Feinberg, Hadar, et al., "Structural Basis for Selective Recognition of Oligosaccharides by DC-SIGN and SC-SIGNR," *Science*, 294, pp. 2163-2166 (2001) (with Supplementary Material published electronically on the*Science* website, 6 pgs.).
Geijtenbeek, et al., "Identification of Different Binding Sites in the Dendritic Cell-Specific Receptor DC-SIGN for Intercellular Adhesion Molecule 3 and HIV-1," *J. Biol. Chem.*, 227(13), pp. 11314-11320 (2002).
Geijtenbeek, Teunis, B.H., et al., "Identification of DC-SIGN, a Novel Dendritic Cell-Specific ICAM-3 Receptor that Supports Primary Immune Responses," *Cell*, 100, pp. 575-585 (2000).
Geijtenbeek, Teunis, B.H., et al., *Cell*, 100, pp. 587-597 (2000).

(Continued)

*Primary Examiner*—Ruixiang Li
(74) *Attorney, Agent, or Firm*—Ropes & Gray LLP

(57) ABSTRACT

The C-type lectin DC-SIGN is absent in normal synovium but is highly expressed by CD68 positive macrophages in the synovium of rheumatoid arthritis patients. Accordingly, rheumatoid arthritis is diagnosed or treated by, respectively, assaying or blocking DC-SIGN. This can be accomplished by the use of agents, e.g., antibodies, which bind specifically to DCSIGN. Agents that bind to ICAM-3 are used to block inhibition of activation of macrophages by DC-SIGN-ICAM-3 interaction and cause inhibition of rheumatoid arthritis symptoms.

7 Claims, 10 Drawing Sheets

OTHER PUBLICATIONS

Gruber, Andreas, et al., "Functional Aspects of Binding of Monoclonal Antibody DCN46 to DC-SIGN on Dendritic Cells," *Immunology Letters*, 84, pp. 103-108 (2002).

Harlow and Lane, Antibodies, A Laboratory Manual, 1988.

Janeway, Charles, A., Jr., et al., *Immunobiology*, (5th ed.), Garland Publishing, New York, p. 691 (2001).

Knight SC., et al., "Bone Marrow-Derived Dendritic Cells, Infection with Human Immunodeficiency Virus, and Immunopathology," Annual Review Immunology 15:593-615 (1997).

Manca F. et al., "Dendritic Cells Are Potent Antigen-Presenting Cells for In Vitro Induction of Primary Human CD4+ T-Cell Lines Specific for HIV GP 120," Journal of Acquired Immune Deficiency Syndromes 7:15-23 (1994).

Package insert for Orthoclone OKT3 Sterile Solution (murumonab-CD3) from Ortho Biotech Products LP, Raritan, NJ, Revised Mar. 2001.

Pohlmann, Stefan, et al., "DC-SIGN Interactions with Human Immunodeficiency Virus Type 1 and 2 and Simian Immunodeficiency Virus," *J. of Virology*, 75(10), pp. 4664-4672 (2001).

Product Information for Affinity Purified anti-human CD209 (DC-SIGN) antibody, from eBioscience, printed on Jan. 5, 2004 from http://www.ebioscience.com/ebioscience/specs/antibody_14/14-2099.htm.

Purified Mouse Anti-Human Monoclonal Antibody, BD PharMingen Technical Data Sheet, BD Biosciences Product Information sheet, Catalog No. 551186, May 1, 2001.

Sequence Alignment of Curtis et al., PNAS 89: 8356-8360 (1992) with SEQ ID No. 2 from U.S. Appl. No. 09/719,961.

Soilleux, E.J., et al., "Cutting Edge: DC-SIGN; a Related Gene, DC-SIGNR; and CD23 Form a Cluster on 19p.13,$_{1,2}$," The Journal of Immunology, 165:2937-2942 (2000).

Steinbrook, R., "One Step Forward, Two Steps Back—Will There Ever Be an AIDS Vaccine?," N. Engl. J. Med., 357:2653-2655 (2007).

Steinman, *Cell*, 287, pp. 491-494 (2000).

Taken, P.J., et al., "Effective induction of naive and recall T-cell responses by targeting antigen to human dendritic cells via a humanized anti-DC-SIGN antibody," Blood, 106(4):1278-1285 (2005).

Toda, et al., *Immunology*, 92, pp. 111-117 (1997).

Tsunetsugu-Yokota, Y. et al., "Efficient Virus Transmission from Dendritic Cells to CD4+ T Cells in Response to Antigen Depends on Close Contact through Adhesion Molecules," Virology 239:259-268 (1997).

Vakeva, Antti, P., et al., "Myocardial Infarction and Apoptosis After Myocardial Ischemia and Reperfusion," *Circulation*, 97, pp. 2259-2267 (1998).

Woodle, E.S., et al., Translplantation, 68, pp. 608-616 (1999).

Yan et al., "β-Glucan, a "Specific" Biologic Response Modifier That Uses Antibodies to Target Tumors for Cytotoxic Recognition by Leukocyte Complement Receptor Type 3 (CD11b/CD18)," The Journal of Immunology, 163(6):3045-3052 (1999).

Zoeteweij, JP. et al., "HIV-Dendritic Cell Interatcions Promote Efficient Viral Infection of T Cells," Journal of Biomedical Science 5:253-259 (1998).

* cited by examiner

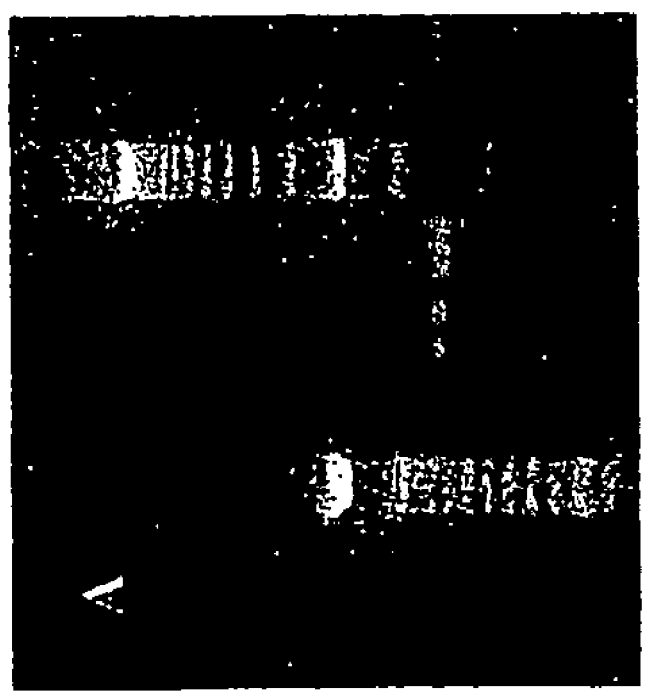
FIGURE 1A
FIGURE 1B

| DC-SIGN | CD68 | DC-SIGN+CD68 |

METHODS OF IDENTIFYING AND ISOLATING CELLS EXPRESSING DC-SIGN

This application is a U.S. National Stage filing of International Application No. PCT/IB2003/005181, filed Sep. 19, 2003, which claims priority to U.S. Provisional Application No. 60/412,624, filed Sep. 20, 2002. All of the foregoing applications are hereby incorporated herein by reference in their entirety.

BACKGROUND

The synovial layer covering the inside of diarthrodial joints forms the main focus of the chronic inflammatory response during rheumatoid arthritis (RA) and is the major producer of pro-inflammatory cytokines and enzymes which cause irreversible cartilage and bone destruction (Klippel, 1997) within this disease. The key cells in the RA synovium mediating tissue damage are thought to be macrophages (Kinne et al., 2000) and synoviocytes (Pap et al., 2000), but also T cell responses may drive part of the synovial inflammation and destruction (Firestein and Zvaifler, 2002).

Rheumatoid arthritis is a chronic inflammatory arthritis that afflicts approximately 1% of adults (Mitchell, 1985). It affects the synovial membrane and leads to irreversible damage of cartilage and bone. The distribution of affected joints is symmetric and typically involves the small articulations of the hands and feet, although the larger appendicular joints like the shoulders and hips are often affected in established disease. Joint deformities, including ulnar deviation of the metacarpal phalangeal joints of the hand or destruction of the weight bearing joints, can occur late in the disease.

The symptoms of the disease result from a massive increase in the number of cells lining the synovium of the joint. The various cell types that are present include type A synoviocytes, which have the characteristics of monocytes or terminally differentiated macrophages, and type B synoviocytes, which are fibroblast-like. As these cells increase in number, the continuous inflammation causes initial symptoms. Eventually, local release of enzymes by the synovial internal lining degrades the extracellular matrix and causes deformity. The mainstays of therapy for rheumatoid arthritis include non-steroidal anti-inflammatory drugs, injectable gold salts, immunosuppressive agents, and methotrexate. While controlled studies do show some clinical benefit from these drugs, improvement is often limited and toxicity is common. Furthermore, most data suggest that these agents do not halt the rate of cartilage or bone destruction. Hence, a novel treatment that is directed at the pathogenesis of the disease with potential disease modifying activity would be a major improvement. The origin of the cells in the hyperplastic synovial lining in chronic inflammatory joint diseases remains controversial. Necrosis and apoptosis are two basic processes by which cells may die. In necrosis cell death usually is a result of cell injury. The cells tend to swell and lyse, and the cell contents ultimately spill into the extracellular space. By contrast, apoptosis is a mode of cell death in which single cells are deleted in the midst of living tissues. Apoptosis accounts for most of the programmed cell death (PCD) in tissue remodeling and for the cell loss that accompanies atrophy of adult tissues following withdrawal of endocrine and other growth stimuli. In addition, apoptosis is believed to be responsible for the physiologic death of cells in the course of normal tissue turnover (i.e., tissue homeostasis) (Kerr et al., 1972; Wyllie et al., 1980).

The most abundant cell type present in RA synovium is the macrophage. The majority of synovial macrophages are thought to arise from monocytes which infiltrate into the synovium where they mature into tissue macrophages and dendritic cells (DC) under influence of growth factors like GM-CSF and IL-4 (Jonuleit et al., 1996). Synovial macrophages become activated by as yet unknown factors.

Macrophage antigens/lectins play an important role in the recognition and destruction of foreign and diseased cells. The selective modulation of the expression and specificity of a novel human macrophage antigen may allow the successful management of diseases related to macrophage function.

Macrophages are bone marrow-derived cells that form an important part of the host defense system. They play a role in physiological as well as pathological processes, such as inflammation, fibrosis atherogenesis, and tumor invasion.

Macrophages are relatively large (10-20 μm), long-lived, amoeboid, phagocytic and pinocytotic cells present in blood, lymph and other tissues. They are derived from monocytes which form a pool of precursors migrating from blood into peripheral tissues such as liver, spleen, lung, lymph nodes, peritoneum, skin, brain and bone, where they differentiate into macrophages with organ specific features. Macrophages play important roles in host resistance to a variety of pathogenic microorganisms, having important functions in, for example, phagocytosis, inflammation, antibody formation, cell-mediated cytotoxicity and delayed hypersensitivity.

In this regard, the major characteristic of macrophages is their ability to recognize, internalize and destroy a variety of foreign and endogenous substances and, thus, to function as scavengers that engulf pathogenic organisms, such as bacteria, parasites and viruses. Macrophages also remove extravasated blood cells or dead cells in tissues and, thereby, participate in the maintenance of tissues. Furthermore, macrophages are thought to play a role in immune response by presenting foreign antigens (i.e., are antigen-presenting cells) to lymphocytes. The macrophages have been shown to be able to bind "nonself" pathogens directly, or they recognize pathogens as foreign because they have been coated by antibodies or complement. The exact recognition mechanism is unknown, but it has been proposed that receptors with broad binding specificity are used to discriminate between self and nonself.

Activated synovial macrophages are the main producers of IL-1 (van den Berg and van Lent, 1996) and TNFα (Feldmann et al., 1996). Recent studies suggest that interfering with the function of these cytokines is an effective approach for therapy in human RA (Feldmann et al., 1996; Bresnihan et al., 1998). Furthermore, cartilage and bone degrading enzymes like matrix metalloproteinases (MMPs) and serine proteinases are also produced (Katrib et al., 2001) by macrophages and the amount of these cells in the synovium appeared to be strongly correlated to severity of the cartilage destruction (Mulherin et al., 1996; Yanni et al., 1994).

Apart from macrophages, T cells extensively infiltrate the RA synovium. Although a plethora of antigens have been suggested as a possible cause of this disease, the relationship between T cell reactivity and pathogenesis remains obscure. Most T cells lack the morphology, surface phenotype and cytokine secretion profile of T cell blasts (Fox, 1997). Furthermore levels of IL-2 in the synovium are low (Firestein and Zvaifler, 1990) and only a small minority of synovial T cells express IL-2Rs (Fox et al., 1990) which suggests that the number of active T cells is low within the synovium. In contrast, naive (CD45RA) and memory (CD45RO) resting T cells are extensively found within RA synovium (Summers et al., 1994) but their presence is thought to be an epiphenomenon. In vitro studies have shown that interaction between resting T cells and monocytes (Dayer and Burger, 1994) or fibroblasts (Chizzolini et al., 2000) may be involved in cell activation and elevated release of cytokines and enzymes. Which surface receptors are important in the synovial naive T cell-macrophage interaction remains to be discovered.

Naive T cells are characterized by a high expression of ICAM-3 which is a member of the IgG supergene family and is rapidly downregulated after activation (Vazeux et al., 1992). Recently a novel ICAM-3 binding C-type lectin, known as DC-SIGN, expressed by dendritic cells in tissues of healthy donors was found. It was observed that DC-SIGN mediates adhesion between dendritic cells and ICAM-3 on naive T cells and appears to be essential for DC-induced T cell proliferation (Geijtenbeek et al., 2000; Steinman, 2000).

WO 00/63251 describes DC-SIGN, which binds ICAM receptors on the surface of T cells. Modulation of immune responses can be achieved by affecting the interaction between dendritic cells and T cells. Immune responses can be inhibited or prevented by preventing the interaction of DC-SIGN on dendritic cells with receptors on T cells, e.g., by using antibodies specific for DC-SIGN. Alternatively, an immune response to an antigen can be potentiated by binding the antigen to DC-SIGN on dendritic cells such that the antigen plus DC-SIGN is taken up by dendritic cells and processed and presented to T cells. The contents of WO 00/63251 are specifically incorporated herein by reference in their entirety.

WO 96/23882 describes a murine and human receptor with C-type lectin domains that is abundantly expressed on the surface of dendritic cells and thymic epithelial cells. The murine receptor—named "DEC-205"—is described as a 205 kDa protein with an isoelectric point of about 7.5 that contains 10 C-type lectin domains and that is homologous to the macrophage mannose receptor (MMR).

WO 96/23882 further describes monoclonal and polyclonal antibodies against DEC-205. However, these antibodies were not able to block dendritic cell function. In particular, monoclonal and polyclonal anti-DEC-205 antibodies were unable to inhibit the interaction between dendritic cells and helper T cells, both in vitro (as determined by the inability of anti-DEC-205 to inhibit allogenic T cell proliferation in a one way mixed leukocyte reaction) and in vivo (as determined by the inability of anti-DEC-205 to inhibit an in vivo response, i.e. in a local graft-versus-host (GVH) reaction). These results suggest that the DEC-205 receptor is not involved in dendritic cell-T-cell interaction (i.e. adhesion) and that the anti-DEC-205 antibodies cannot be used to modulate the immune response.

Curtis et al. (1992), as well as in WO 93/01820, describe a non-CD4 gp120 receptor isolated and cloned from human placenta tissue. This gp120 receptor is expressed on mammalian cells which do not exhibit high levels of CD4, such as placenta, skeleton muscle, brain, neural and mucosal cells, as well as other tissues and cells including colon, thymus, heart, T cells, B cells and macrophages (but not in the liver or the kidney). The amino acid sequence of the C-type lectin gp120 receptor disclosed in SEQ ID NOs:1 and 2 of WO 93/01820 has a high degree of sequence homology (>98%) with the C-type lectins that were found to be present on dendritic cells (WO 00/63251; Geijtenbeek et al., 2000).

Curtis et al. (1992) and WO 93/01820 further discuss the role this C-type lectin receptor plays in the infection of the aforementioned cells/tissues with HIV, i.e. by binding the major HIV envelope glycoprotein gp120 prior to internalization of the virion into the cell. It was found that inhibition of the C-type lectin gp120 receptor could reduce or inhibit HIV infection of these cells/tissues. As suitable inhibitors, WO 93/01820 discloses mannose carbohydrates, fucose carbohydrates, plant lectins such as concanavalin A, specific antibiotics such as pradimicin A, and sugars such as N-acetyl-D-glucosamine and galactose (which however are described as less potent). These compounds and compositions containing them are used either in vitro or in vivo to inhibit the binding of HIV to the cell surface.

WO 93/01820 further discloses that binding of HIV to COS-7 cells can be inhibited by pre-incubation of gp120 with an anti-gp120 monoclonal antibody (named "antibody 110.1"). However, this antibody is not directed against the C-type lectins, but against the gp120 protein.

Neither Curtis et al. (1992) nor WO 93/01820 mentions or suggests the presence of such a C-type lectin on dendritic cells or on macrophages, nor do these references mention or suggest their role in dendritic cell—T cell interaction during the initial stages of an immune response nor in macrophage—T cell interaction in rheumatoid arthritis.

WO 95/32734 describes FcγRII (CD32) bridging (or crosslinking) compositions and their use in modulating the immune response to specific antigens. This reference is based upon the finding that the bridging of FcγRII (CD32) molecules on antigen presenting cells (APCs) impairs the expression of the essential co-stimulatory molecules B7-1/2 (i.e. prevents their up-regulation) and thereby impairs the expression of (i.e. causes the down-modulation of) the adhesion molecule ICAM-3, with the functional consequence of an impaired capacity of the monocytes to co-stimulate the activation of antigen-specific T cells (i.e. resulting in the modulation of antigen-specific T cell unresponsiveness). The bridging agent is chosen from aggregated human IgG molecules or Fc-fragments thereof; bi- or multivalent monoclonal antibodies to FcγRII or fragments thereof, or a fusion of two or more human IgG Fc parts.

WO 95/32734 is directed towards modulating (i.e. inhibiting) the co-stimulation signal required for T cell activation (i.e. besides the primary signal of TcR/CD3 interaction), in particular to induce proliferation and maturation into effector cells. WO 95/32734 is not directed towards modulating dendritic cell—T cell adhesion or macrophage—T cell adhesion, nor does it disclose or suggest either the presence of C-type lectins on the surface of dendritic cells or macrophages in persons with rheumatoid arthritis or their interaction with the ICAM-3 receptors on T cells.

WO 98/02456 discloses a group II human C-type lectin isolated from a stimulated human macrophage library. WO 98/49306 discloses a group IV C-type lectin present in human pancreatitis-associated protein ("PAP"). WO 98/41633 discloses a group V human C-type lectin isolated from a human tumor clone.

WO 98/02456, WO 98/49306 and WO 98/41633 further disclose methods for producing antibodies against these C-type lectins. However, none of these references relates to C-type lectins on macrophages in persons with rheumatoid arthritis.

Dendritic cells (DC) are professional antigen-presenting cells that capture antigens in the peripheral tissues and migrate via lymph or blood to the T cell area of draining lymph nodes and spleen. Here they present processed antigens to naive T cells, initiating antigen-specific primary T cell responses.

DC are unique in their ability to interact with and activate resting T cells. However, prior to publication of WO 00/63251 and Geijtenbeek et al. (2000), it was largely unknown how DC-T cell contact is initiated and regulated. Therein, the role of ICAM-3 in DC-T cell interactions was investigated. It was demonstrated that although DC strongly adhere to ICAM-3, this adhesion is not mediated by LFA-1, αD or any other integrin. In the search for this novel ICAM-3 receptor on DC a C-type lectin receptor was cloned, designated DC-SIGN, which is preferentially expressed by DC. Besides its prominent role in DC-T cell clustering and initiation of T cell responses, it was discovered that DC-SIGN is a major HIV-1 receptor involved in infection of DC and subsequent HIV-1 transmission to T cells. Thus HIV-1 and resting T cells exploit a similar highly expressed receptor to interact with DC.

The publications and other materials used herein to illuminate the background of the invention, and in particular, cases to provide additional details respecting the practice, are incorporated herein by reference and, for convenience, are referenced by author and date in the text and respectively grouped in the appended List of References.

SUMMARY

In one aspect it has been found that DC-SIGN is highly expressed on macrophages in the synovium of rheumatoid arthritis patients. This expression of DC-SIGN is not seen in either control patients or in patients with osteoarthritis.

A further aspect provides methods for treating patients who have rheumatoid arthritis, said method comprising the use of compounds that interfere with the interaction of DC-SIGN and its ICAM-3 receptor.

Another aspect involves a method for diagnosing the presence of rheumatoid arthritis in a person by determining the percentage of cells in the synovium of said person that is expressing DC-SIGN.

In addition methods for isolating macrophages from persons with rheumatoid arthritis are described.

BRIEF DESCRIPTION OF THE DRAWINGS

FIGS. 1A-B show DC-SIGN expression (mRNA and protein) determined in RA synovial specimens using RT-PCR and immunolocalization. FIG. 1A shows the results of amplifying mRNA, isolated from synovial specimens and dendritic cells, via PCR. Lanes 1 and 4 are molecular size markers, lane 2 shows the results from dendritic cells, and lane 3 shows the results from RA synovium. FIG. 1B represents immunolocalization on a cryostat section of synovia from an RA patient using a specific anti-DC-SIGN antibody.

FIG. 4A shows staining with anti-CD68. FIG. 4B shows staining with anti-DC-SIGN. FIGS. 4C-E show double labeling experiments (anti-DC-SIGN in FIG. 4C, anti-CD68 in FIG. 4D, and both anti-CD-SIGN and anti-CD68 in FIG. 4E).

BRIEF DESCRIPTION OF THE SEQUENCE LISTING

Figure 2A:
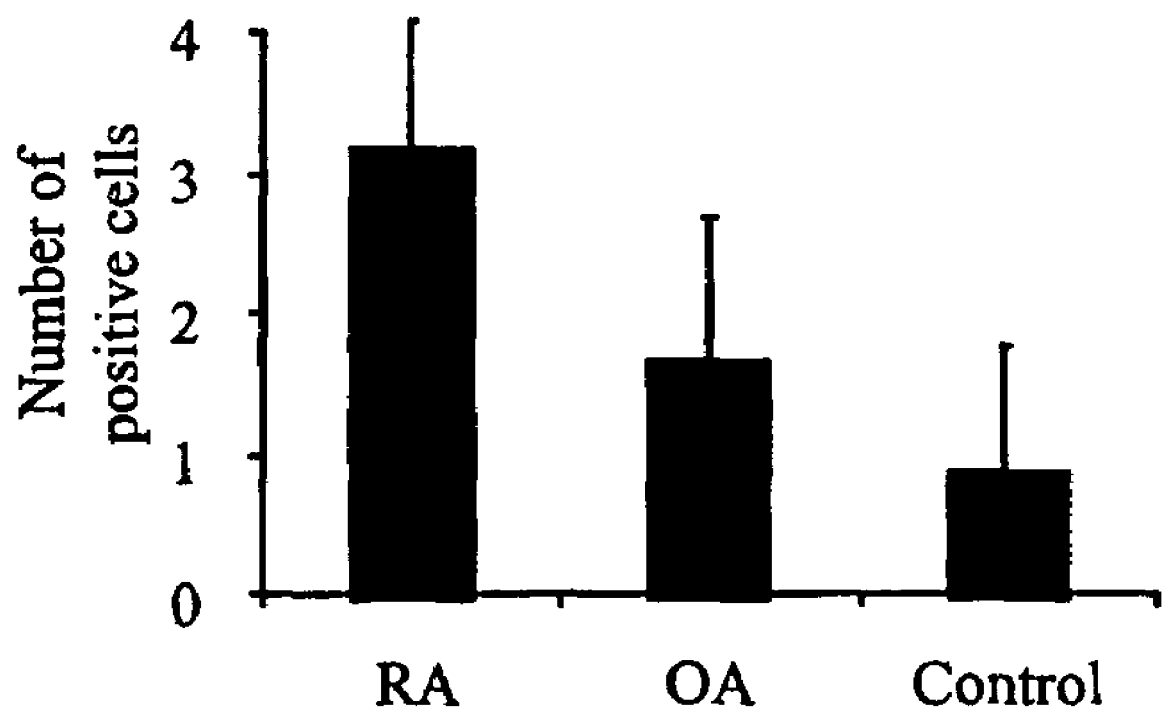
FIG. 2A shows the number of inflammatory cells in the synovia of RA, OA and trauma patients expressing DC-SIGN scored using an arbitrary scale from 0-4 (0=no cells, 1=0-25%, 2=25-50%, 3=50-75% and 4=75-100%).

SEQ ID NO:1 is a nucleic acid sequence encoding DC-SIGN.
SEQ ID NO:2 is the amino acid sequence of DC-SIGN.
SEQ ID NO:3 is a sense primer for PCR amplification of DC-SIGN.
SEQ ID NO:4 is an antisense primer for PCR amplification of DC-SIGN.
SEQ ID NO:5 is a sense primer for PCR amplification of GAPDH.
SEQ ID NO:6 is an antisense primer for PCR amplification of GAPDH.

DETAILED DESCRIPTION OF PREFERRED EMBODIMENTS

In accordance with the present disclosure, DC-SIGN expression in synovial inflammation is now shown to be present in RA, whereas DC-SIGN expression is lacking in osteoarthritis (OA) and trauma synovia. Furthermore, a relationship between DC-SIGN positive cells and ICAM-3 positive naive T cells is shown. In addition, DC-SIGN positive cells are characterized in terms of phenotype (DC/macrophage markers) and it is shown that EMPRINN/MMP is found in close proximity. The results indicate that in rheumatoid arthritis, but not in osteoarthritis or control samples, macrophages are present that express DC-SIGN. These macrophages are found in close association with ICAM-3 expressing T cells and also with the cartilage degrading proteins EMPRINN and MMP-1. Accordingly, RA can be diagnosed by assaying for the presence of DC-SIGN positive macrophages in synovium. Additionally, RA patients are treated by blocking the interaction of macrophages and T cells by blocking DC-SIGN or its ICAM-3 receptor.

It is shown herein that DC-SIGN receptor is extensively expressed on both CD68 expressing tissue macrophages and dendritic cells present in the synovium of RA patients. The majority of synovial macrophages seen during RA are the product of a maturation process of infiltrated blood monocytes and DC-SIGN induction is a result of local cytokine production, as confirmed by the present finding that the high number of DC-SIGN positive cells in the synovium was not due to enhanced expression of these cells in peripheral blood but is rather induced by local factors in the tissue.

ICAM-3 is a specific ligand of DC-SIGN (Geijtenbeek et al., 2000). ICAM-3 expressing naive CD45RA T cells are abundantly present within RA synovia. The results presented herein show a clear association between the number of DC-SIGN positive macrophages/DC, the presence of ICAM-3 positive T cells, and EMPRINN and MMP-1 (collagenase). MMP producing macrophages have been shown to be highly involved in irreversible breakdown of the collagen type II matrix of the cartilage during RA (Cawston, 1998). Although a significant contribution of T cells to joint pathology in the RA joint could not be proven up to now, adoptive transfer of CD4 positive T cells into NOD-SCID mice engrafted with rheumatoid synovial tissue leads to high expression of TNFα and MMP-1 and MMP-2 (Wernicke et al., 2002).

In addition ICAM-3 is also expressed in a soluble form. Expression of soluble and cell surface ICAM-3 is preferentially seen in the state of low activation of the immune system (Nassonov et al., 2000). Soluble ICAM-3 (sICAM-3) is detected in the circulation of healthy individuals (Nassonov et al., 2000) and elevated in immune mediated diseases like Guillain-Barre syndrome, multiple sclerosis, SLE, psoriasis and also RA. Elevated levels of sICAM-3 are present in sera and synovial fluids of RA patients (Szekanecz et al., 1994). sICAM-3 in the synovial fluid was strongly correlated to synovial fluid leukocyte counts whereas in vitro, synovial fluid mononuclear cells produce sICAM-3 spontaneously (Hosaka et al., 1996).

In comparison with RA, the synovium derived from OA patients is significantly less infiltrated by MMP producing inflammatory cells. Since DC-SIGN was expressed at low levels by OA synovial macrophages and only few CD45RA T cells were present, macrophage/T cell interactions were virtually absent. Furthermore, sICAM-3 is hardly observed in synovial fluid of OA patients (el-Gabalawy et al., 1994) whereas apoptotic cells were equally rare. From these findings it is seen that ICAM-3-DC-SIGN interactions are only observed during chronic inflammation when MMP is present in the synovium.

Depleting T cells using monoclonal antibodies or immunotoxins against activated CD4 positive T cells has generally been disappointing (Schulze-Koops and Lipsky, 2000; Panayi, 1999). These monoclonal antibodies leave the majority of naive CD45RA T cells unharmed.

Activated macrophages have been shown to be very important in chronic inflammation and cartilage and bone destruction (Barrera et al., 2000; Yanni et al., 1994). The present study shows that during RA, DC-SIGN is expressed on synovial macrophages and can be an important receptor involved in MMP production after interaction with naive CD45RA T cells and therefore the DC-SIGN receptor is a new target to combat this crippling disease.

In view of the above information, and further supported by the Examples below, it is seen that activation of macrophages by interaction of DC-SIGN and ICAM-3 at least partially results in the symptoms of rheumatoid arthritis. Inhibition of the activation of DC-SIGN positive macrophages in the synovium of RA patients will aid in limiting the symptoms of RA. Inhibition can be accomplished by preventing the interaction between DC-SIGN and ICAM-3. Agents that bind to either DC-SIGN or to ICAM-3 can inhibit the interaction. Such agents can include, but are not limited to, those DC-SIGN binding agents as set forth WO 93/01820 and WO 00/63251. These include mannose and fucose carbohydrates, plant lectins such as concanavalin A, antibiotics such as pradimicin A, sugars such as N-acetyl-D-glucosamine and galactose, and antibodies to DC-SIGN such as AZN-D1 and AZN-D2. Antibodies against ICAM-3 can also be used for this therapeutic purpose.

Compounds that can be used in the compositions of the invention include inhibitors for the C-type lectins known per se, including but not limited to those described in WO 93/01820 as mentioned above.

In general, these are compounds that can bind or adhere to, preferably in a reversible manner, or that can serve as a ligand for, the C-type lectins, in particular the C-type lectin of SEQ ID NO:2 or natural variants or equivalents thereof. Examples are mannose carbohydrates such as mannan and D-mannose; fucose carbohydrates such as L-fucose; plant lectins such as concanavalin A; antibiotics such as pradimicin A; sugars such as N-acetyl-D-glucosamine and galactose; as well as suitable peptidomimetic compounds and small drug molecules, which can for instance be identified using phage display techniques. Furthermore, proteins such as gp120 and analogs or fragments thereof or similar proteins with binding capacity to C-type lectins on dendritic cells may be used, as well as isolated ICAM-receptors and analogs thereof, including parts or fragments thereof. Such parts or fragments should then preferably still be such that they can bind to the C-type lectins on the surface of dendritic cells or macrophages.

Although they can be used, the use of carbohydrates is usually less desired from a therapeutic point of view, as they can be rapidly metabolized in vivo. Also, the use of plant lectins such as concanavalin A and pradimicin antibiotics can have disadvantages in a therapeutic setting, in particular when treating patients with autoimmune disorders and/or HIV infections.

Preferably, one or more physiologically tolerable and/or pharmaceutically acceptable compounds are used, such as defined in WO 93/01820, incorporated herein by reference. For instance, the use of gp120 or derivatives thereof may cause undesired side effects, in particular on the nervous system (vide WO 93/01820).

Therefore, it is preferred that an antibody directed against a C-type lectin as present/expressed on the surface of a dendritic cell or a macrophage, or a part, fragment or epitope thereof, is used. As used herein, the term antibodies includes inter alia polyclonal, monoclonal, chimeric and single chain antibodies, as well as fragments (e.g., Fab, F(ab')$_2$, F(ab'), Fv, Fd) and an Fab expression library. Furthermore, "humanized" antibodies may be used, for instance as described WO 98/49306, incorporated herein by reference.

Such antibodies against the C-type lectins of the invention can be obtained as described hereinbelow or in any other manner known per se, such as those described in WO 95/32734, WO 96/23882, WO 98/02456, WO 98/41633 and/or WO 98/49306, each incorporated herein by reference.

For instance, polyclonal antibodies can be obtained by immunizing a suitable host such as a goat, rabbit, sheep, rat, pig or mouse with a C-type lectin or an immunogenic portion, fragment or fusion thereof, optionally with the use of an immunogenic carrier (such as bovine serum albumin or keyhole limpet hemocyanin) and/or an adjuvant such as Freund's, saponin, ISCOM's, aluminum hydroxide or a similar mineral gel, or keyhole limpet hemocyanin or a similar surface active substance. After an immune response against the C-type lectins has been raised (usually within 1-7 days), the antibodies can be isolated from blood or serum taken from the immunized animal in a manner known per se, which optionally may involve a step of screening for an antibody with desired properties (i.e. specificity) using known immunoassay techniques, for which reference is again made to, for example, WO 96/23882.

Monoclonal antibodies may be produced using continuous cell lines in culture, including hybridoma and similar techniques, again essentially as described in the above cited references.

Fragments such as F(ab')$_2$ and Fab may be obtained by digestion of an antibody with pepsin or another protease, reducing disulfide-linkages and treatment with papain and a reducing agent, respectively. Fab-expression libraries may for instance be obtained by the method of Huse et al. (1989).

Preferably, a monoclonal antibody against the C-type lectin(s) on dendritic or macrophage cells is used, more specifically against the peptide with the amino acid sequence shown in/encoded by SEQ ID NOs:2 and 1 or an antigenic part thereof. Although two monoclonal antibodies, herein referred to as AZN-D1 and AZN-D2, are illustrated herein, those skilled in the art can generate functional monoclonal antibodies with comparable specificity for C-type lectins. Hybridomas that produce the abovementioned monoclonal antibodies AZN-D 1 and AZN-D2 of the invention were deposited on Apr. 8, 1999 with the European Collection of Cell Cultures (ECACC), Centre for Applied Microbiology and Research, Porton Down, Salisbury, Wiltshire SP4 0JG, United Kingdom, under ECACC accession numbers 99040818 and 99040819, respectively.

This disclosure also relates to a method for producing an antibody, preferably a monoclonal antibody, against the C-type lectins on macrophage cells, said method comprising cultivating a cell or a cell line that produces said antibody and harvesting/isolating the antibody from the cell culture.

Antibodies against the C-type lectins on dendritic cells have been described by WO 00/63251, incorporated herein by reference, and it is envisaged that those antibodies will have broad applicability (i.e. besides the pharmaceutical/therapeutic uses disclosed herein) against these same C-type lectins on macrophages.

Antibodies against C-type lectins can be used to detect the presence of, and thereby determine the expression of, C-type lectins in or on tissues or whole cells, as well as to detect the presence of C-type lectins in other biological samples such as cell fragments or in cell preparations. The information thus obtained can then be used to determine whether a condition exists that can be treated in accordance with the present disclosure. The C-type lectin antibodies are also used to detect (qualitatively and/or quantitatively), isolate, purify and/or produce macrophage cells, especially CD68 macrophages, for instance in/from biological samples, including biological fluids such as blood, plasma or lymph fluid; tissue samples or cell samples such as bone marrow, skin tissue, tumor tissues, etc; or cell cultures or cultivating media.

By using C-type lectin monoclonal antibodies as disclosed herein, desired macrophage cells can be isolated and produced with high yield and with high specificity. In such a method, the monoclonal antibodies can be used in a manner known per se for the harvesting, isolation and/or purification of cells from biological fluids using antibodies.

For instance, the monoclonal antibodies are attached to a column, or matrix, to magnetic or paramagnetic beads or to a similar solid support, which could then be contacted with a biological sample or culture medium containing macrophages. The cells that do not attach themselves to the carrier are then separated or removed, e.g. by washing, after which the macrophage cells are separated from the carrier and isolated in a manner known per se.

Also, the C-type monoclonal antibodies are used to detect/determine the presence of macrophage cells, particularly CD68 macrophage cells, and/or C-type lectins and/or the expression of genes coding therefor in biological samples, in which the antibodies could again be used in a manner known per se for the analysis of antibodies, such as competitive inhibition assays or ELISA-type immunoassays. For instance, the antibodies can be used in combination with microscopy techniques, cell sorting techniques including flow-cytometry and FACS, techniques based upon solid supports and/or detectable labels or markers which can be attached to the antibodies, techniques based upon magnetic or paramagnetic beads or any other detection or assay technique known per se in which antibodies can be used. Such assays and kits, which besides the antibodies of the invention can contain all further components known per se for antibody-based assays, as well as manuals, etc., form a further aspect of the invention.

Thus, the C-type lectin monoclonal antibodies constitute a very useful diagnostic and research tool, for use both in vitro as well as in vivo. Possible non-limiting fields of application include the study of macrophage cells and their function and interactions; the study of the immune system; the detection of macrophage cells and/or C-type lectins in cells, tissues or biological fluids such as synovial tissue; as well as the study of the role macrophages play in biological processes or disease mechanisms, such as arthritis.

For a further description of the methods and techniques known per se in which the antibodies of the invention can be used, reference is made to the general textbooks, such as Sites et al., *Basic and clinical immunology*, 8th Ed., Prentice-Hall (1994) and Roitt et al., *Immunology* 2nd Ed., Churchill Livingstone (1994), which are incorporated herein by reference. Particular reference is made to the general uses of antibodies and techniques involved therein as mentioned in sections 2.7 to 2.17 of the general reference work by Janeway-Travers, *Immunobiology, the immune system in health and disease*, Third Edition, which is incorporated herein by reference.

A useful composition herein may contain two or more of the above-mentioned active compounds, or such compounds may be used in combination. For instance, an anti-C-type lectin antibody can be formulated with mannose or fucose carbohydrates, lectins and/or antibiotics such as pradimicin A, whereby a synergistic effect may be obtained.

Useful compositions may also contain or be used in combination with known co-inhibitory compounds, such as anti-LF3A; as well as other active principles known per se, depending upon the condition to be treated. For instance, the compositions may be formulated or used in combination with immunosuppressants or immunomodulants.

The compositions can further be formulated using known carriers and/or adjuvants to provide a pharmaceutical form known per se, such as a tablet, capsule, powder, freeze dried preparation, solution for injection, etc., preferably in a unit dosage form. Such pharmaceutical forms, their use and administration (single or multi dosage form), as well as carriers, excipients, adjuvants and/or formulants for use therein, are generally known in the art and are for instance described in WO 93/01820, WO 95/32734, WO 96/23882, WO 98/02456, WO 98/41633 and/or WO 98/49306, all incorporated herein by reference. Furthermore, the formulation can be in the form of a liposome, as described in WO 93/01820.

Pharmaceutical formulations of antibodies, their administration and use, are generally described in WO 95/32734, WO 96/23882, WO 98/02456, WO 98/41633 and/or WO 98/49306.

The compositions of the invention may further be packaged, for instance in vials, bottles, sachets, blisters, etc.; optionally with relevant patient information leaflets and/or instructions for use.

In a further aspect a method for modulating the immune response in an animal is described, in particular a human or another mammal, which includes administering to said animal a compound that binds or can bind to a C-type lectin on the surface of a macrophage, preferably in the form of a composition as described above, in an amount sufficient to alter or modify an immune response.

The compound or composition is in particular administered in such an amount that the interaction(s) between macrophages and T cells are altered or modified, more in particular in such an amount that the adhesion of macrophages to T cells is reduced.

In all the above methods and embodiments, the compounds/compositions used will be administered in a therapeutically effective amount, for which term reference is generally made to WO 93/01820, WO 95/32734 and/or WO 96/23882, incorporated herein by reference. The administration can be a single dose, but is preferably part of a multidose administration regimen carried out over one or more days, weeks or months.

All terms used herein have the normal meaning in the art, for which reference can be made to inter alia the definitions given in WO 93/01820, WO 95/32734, WO 96/23882, WO 98/02456, WO 98/41633 and/or WO 98/49306, analogously applied.

Furthermore, although the present disclosure relates to the specific 44 kDa C-type lectin receptor disclosed herein, it is not excluded that other, generally similar C-type lectins, including natural variants of the sequence of SEQ ID NO:2, may also be present on macrophages and/or may be involved in macrophage—T cell interaction. Such variants will usually have a high degree of amino acid homology (more than 80% to more than 90%) with, and/or be functionally equivalent to the specific C-type lectin disclosed herein. Also, any such receptor will generally display properties similar to those as described herein; in particular that inhibition of this receptor, either by carbohydrate inhibitors or specific antibodies, will lead to an alteration of macrophage/T-cell interaction. Any such variant receptors should however be distinguished from the C-type lectin receptor disclosed in WO 96/23882, inhibition of which does not result in inhibition of the interaction of dendritic cells and T-cells and therefore should not result in inhibition of the interaction of macrophages and T-cells.

DC-SIGN Expression in RA Synovium

Figure 2B:
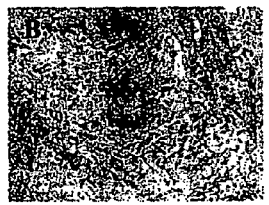
FIGS. 2B-D show DC-SIGN expression in synovia derived from RA (FIG. 2B), OA (FIG. 2C) and trauma patients (FIG. 2D). DC-SIGN expression was investigated using immunolocalization.
Figure 2C:
Figure 2D:
Figure 3A:
FIGS. 3A-D show a comparison of DC-SIGN and other DC-markers. Serial cryostat sections of RA synovia were stained with DC cell specific antibodies against: DC-LAMP (FIG. 3A), FASCIN (FIG. 3B), CD83 (FIG. 3C) and DC-SIGN (FIG. 3D).
Figure 3B:
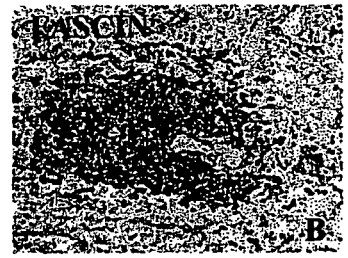
Figure 3C:
Figure 3D:

DC-SIGN was detected in cryostat sections of synovial specimens using a DC-SIGN specific monoclonal antibody (AZN-D1). Immunolocalization was performed on cryostat sections of synovia from ten different RA patients using the anti-DC-SIGN specific antibody AZN-D1. A representative section is shown in FIG. 1B. Seventy percent of the inflammatory cells present expressed DC-SIGN. The DC-SIGN positive cells were found mainly in the deeper lying subintima but also in the superficial lying intima (FIG. 1B). Although DC-SIGN was found throughout the sublining layer, concentrations of positive cells were found in and around lymphocyte aggregates, which surround the blood vessels. The level of DC-SIGN expression was clearly variable between RA patients and correlated with the amount of inflammation. When inflammatory cells were present in OA and trauma synovia, DC-SIGN immunoreactivity was also widespread but these cells stained less intensely when compared to the inflammatory cells found within RA synovium (FIGS. 2 A-D). The number of inflammatory cells in the synovia expressing DC-SIGN was scored using an arbitrary scale from 0-4 (0=no cells, 1=0-25%, 2=25-50%, 3=50-75% and 4=75-100%). DC-SIGN was mainly expressed in synovia of RA patients (FIGS. 2A-B). However when OA (FIGS. 2A and 2C) or trauma synovia (FIGS. 2A and 2D) contained inflammatory cells, they also expressed DC-SIGN although significantly less if compared to RA synovium. Synovia of 10 RA patients were compared with synovia of five OA and five trauma patients.

To confirm the presence of DC-SIGN mRNA in synovial membrane samples, 5 RA samples were studied using RT-PCR. mRNA was isolated from synovial specimens and from dendritic cells. The dendritic cells were derived by culturing human monocytes in the presence of GM-CSF and IL-4 and were used as positive DC-SIGN control (lane 2 of FIG. 1A). Five different patients were investigated. DC-SIGN mRNA was found in all RA synovial membrane samples that were studied. A representative picture shows the 1237 base pair band in RA synovium after 35 cycles (lane 3 of FIG. 1A). Nucleotide sequencing of the PCR amplification products confirmed the identity of the amplified bands. In all OA and "trauma" synovial samples examined, DC-SIGN mRNA was also present but at a much lower level confirming the results found for the tissue cryostat sections.

In healthy tissues, DC-SIGN is exclusively found on dendritic cells. Therefore, it was investigated whether cells expressing DC-SIGN also expressed other markers characteristic for mature dendritic cells. Serial cryostat sections of RA synovium were cut to compare the pattern of staining with anti-DC-SIGN and three other dendritic cell associated monoclonal antibodies (DC-LAMP, CD83 and fascin). Interestingly, clearly distinct staining patterns were observed indicating that inflamed synovia contain different macrophage/DC subsets (FIGS. 3A-D). Though some of the DC-SIGN positive cells were present around the vessels and in the T cell aggregates, most of the DC-SIGN positive cells were lying in areas distinct from $CD83^+$, $DC-LAMP^+$ or $fascin^+$ cells (FIGS. 3A-D).

Figure 4A:
FIGS. 4A-E show a comparison of DC-SIGN and the macrophage marker CD68 in serial cryostat sections of synovial tissue from RA patients.
Figure 4B:

To further identify DC-SIGN positive cells, serial synovial sections were stained with anti-CD14 and anti-CD68, markers of monocytes and mature macrophages, respectively. As expected, CD68 staining was abundantly present in all RA synovia studied. Serial sections show that the pattern of DC-SIGN staining was comparable to that of CD68 staining (FIGS. 4A-B). Approximately 80% of the CD68 cells also appeared to be DC-SIGN positive (FIG. 4A), indicating that DC-SIGN is expressed by a large subpopulation but not by all synovial macrophages/DC. CD68 positive macrophages expressing DC-SIGN were localized in the outer layer of the T cell aggregates whereas in the more central area of the T cell aggregate, many CD68 positive cells were DC-SIGN negative (FIG. 4B).

Figure 4C:
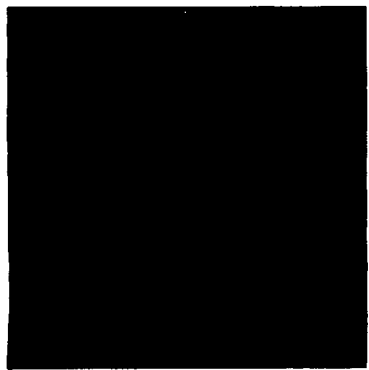
Figure 4D:
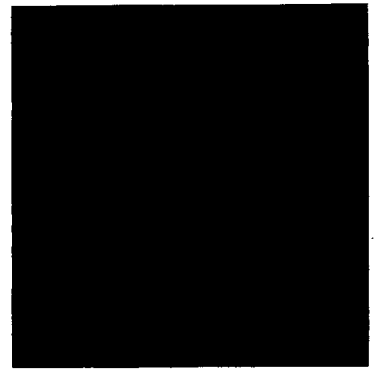
Figure 4E:
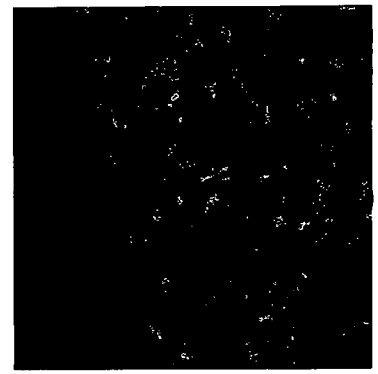

To further prove that CD68 positive cells indeed express DC-SIGN, double labeling immunolocalization studies were performed. The two antigens of interest were visualized by an indirect Alexa 568 labeled CD68 and an indirect Alexa 647 labeled DC-SIGN antibody. It was found that CD68 strongly co-localizes with DC-SIGN (FIGS. 4C-E). Co-localization of DC-SIGN and CD68 was clearly present both in macrophage-like type A lining cells and also in subintimal macrophages (FIGS. 4C-E). Since very low levels of DC-SIGN expressing cells were found in the peripheral blood of seven RA patients and were comparable with the level found in healthy controls, DC-SIGN is likely induced locally in the tissues by as yet unknown local factors released within the synovium of synovial fluid.

Figure 5A:
FIGS. 5A-C show a comparison of DC-SIGN positive cells (FIG. 5A), memory T cells (CD45RO) (FIG. 5B) and naive T cells (CD45RA) (FIG. 5C).
Figure 5B:
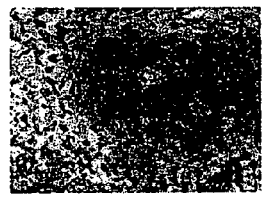
Figure 5C:
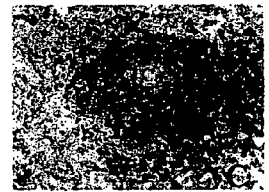
Figure 5D:
FIG. 5D shows the results of a double labeling study showing physical interaction between DC-SIGN positive cells and ICAM-3 expressing naive T cells.

ICAM-3 Expressing Resting T Cells in RA Synovium are in Close Proximity with DC-SIGN As DC-SIGN is a novel dendritic cell receptor which specifically binds to ICAM-3 that is predominantly expressed on naive T cells, the staining pattern of DC-SIGN and several markers for T cells was compared to investigate whether these DC-SIGN positive cells might interact with naive T cells. T cells were identified by anti-CD3, -CD45RA and -CD45RO, which represent a pan-T cell marker and markers for resting naive and memory T cells, respectively. CD3, CD45RA and CD45RO staining was abundant in the lymphocyte aggregates mostly located around blood vessels. Significantly more T cells stained for CD45RA than for CD45RO. These naïve CD45RA cells were found throughout the CD3 positive T cell aggregates. Serial sections showed overlapping staining patterns of DC-SIGN and part of the CD45RA positive cells in the peripheral regions of T cell aggregates (FIGS. 5A-C). Double labeling studies of CD45RA/DC-SIGN and ICAM-3/DC-SIGN in RA synovium sections showed expression of both markers in close proximity to each other indicating that ICAM-3 expressing resting T cells and DC-SIGN expressing macrophages/DC are situated within interacting range (FIG. 5D).

Figure 6A:
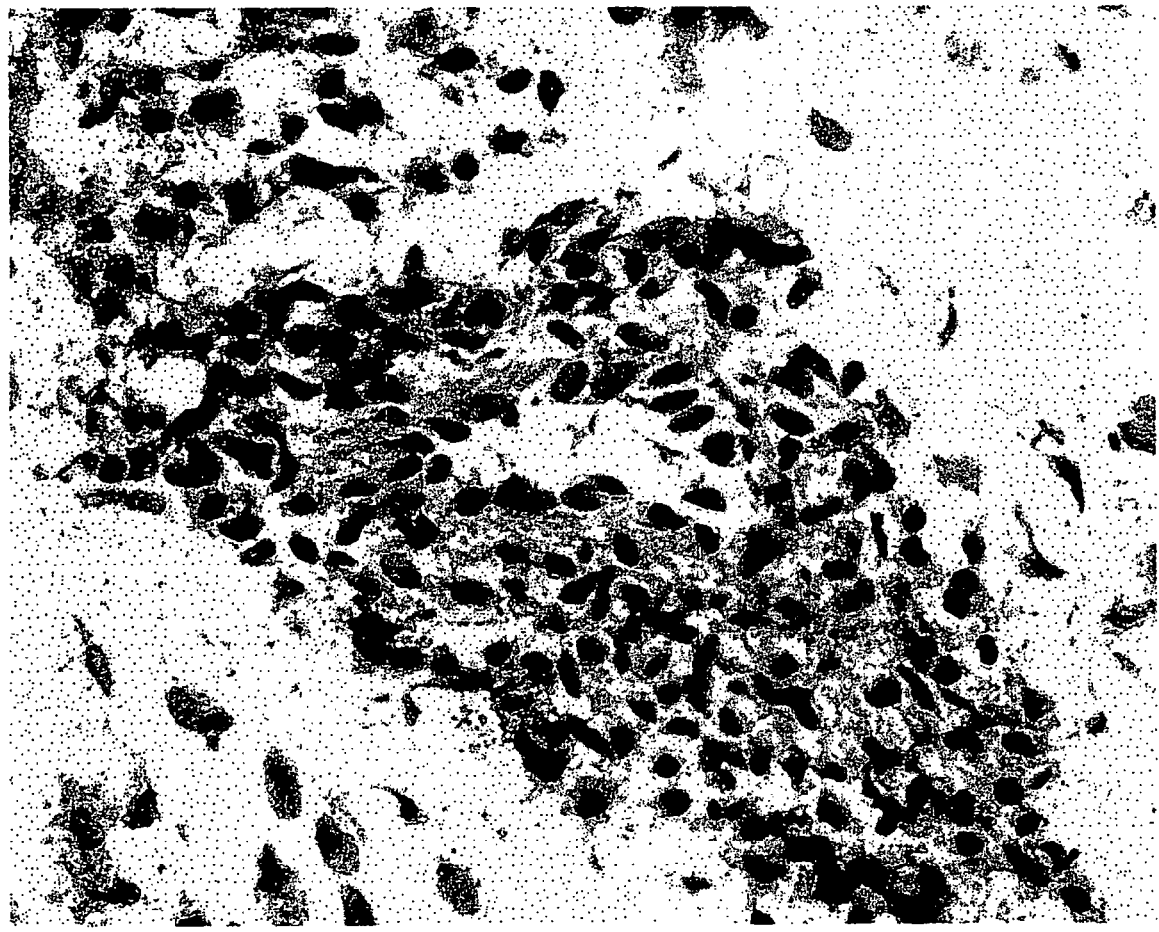
FIGS. 6A-C show a comparison of DC-SIGN, EMPRINN and MMP-1 expression using immunolocalization on serial sections or double staining histochemistry. Expression of MMP-1 on T cell aggregates (FIG. 6A). Expression of EMPRINN (FIG. 6B) and MMP-1 (FIG. 6C) on DC-SIGN positive macrophages lying around T cell aggregates.
Figure 6B:
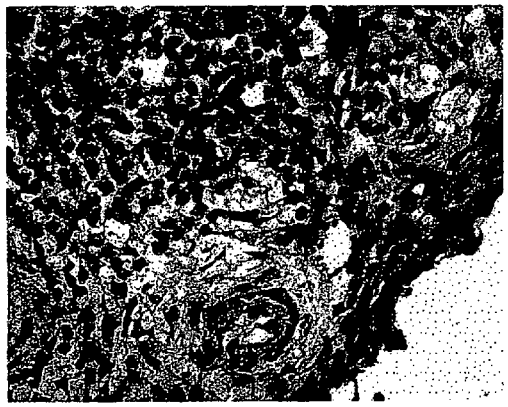
Figure 6C:
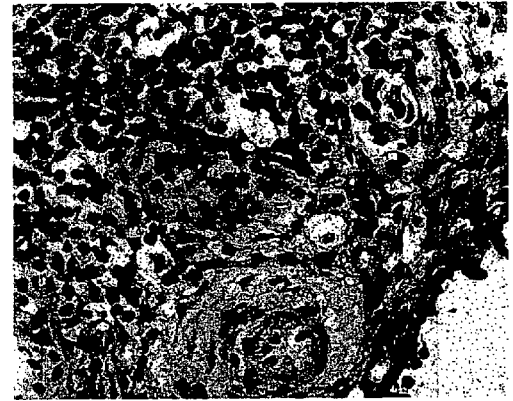

To further investigate whether the physical contact between ICAM-3-T cells and DC-SIGN positive tissue macrophages in the periphery of the T cell aggregate might lead to activation leading to production of cartilage degrading molecules, the expression of MMP-1, which is a crucial enzyme involved in collagen type II breakdown, was investigated. MMP-1 producing cells were particularly found at the periphery of the T cell aggregate (FIG. 6A). Using serial sections it was found that EMPRINN, which is an extracellular MMP-inducer (Tomita et al., 2002), and MMP-1 expression co-localized with areas containing DC-SIGN positive CD68 macrophages that were lying adjacent to T cell aggregates (FIGS. 6B (EMPRINN) and 6C (MMP-1)). DC-SIGN negative but CD68 positive cells lying within the deeper layers of the lymphocyte aggregates failed to express MMP-1 (FIG. 6A).

Figure 7:
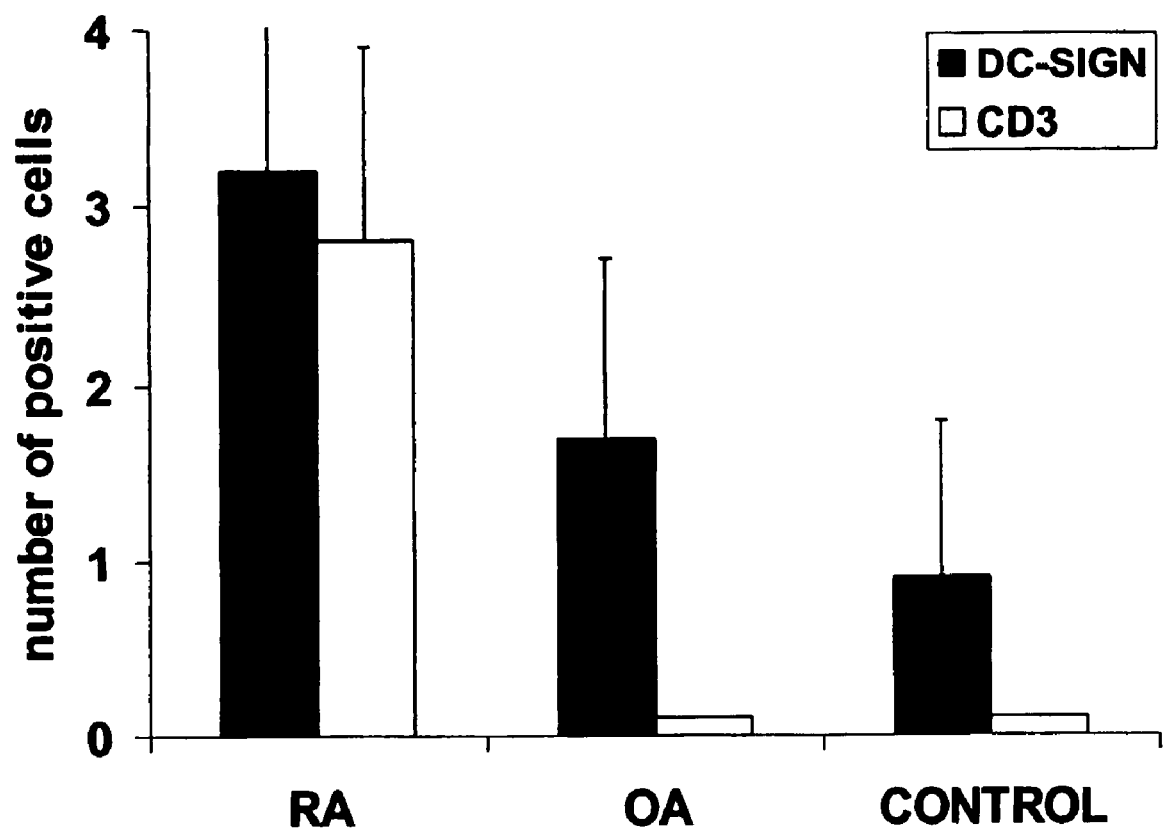
FIG. 7 shows a comparison of DC-SIGN expressing macrophages and T cells (CD3) in synovia of RA, OA and trauma (control) patients.

As lower numbers of DC-SIGN positive cells were also found within OA synovia, the presence of naïve CD45RA T cells was further investigated. Interestingly CD3, CD45RA and ICAM-3 staining were found in only minute amounts in synovia derived from OA and "trauma" patients (FIG. 7 showing CD3 results), demonstrating that interactions between DC-SIGN positive macrophages and ICAM-3 containing resting T cells are significantly less frequent within these synovia due to less expression of DC-SIGN and hardly any expression of ICAM-3. Two observers in a random fashion scored the number of positively stained cells in synovial specimens. The number of cells was measured using an arbitrary scale (as for FIG. 2A). DC-SIGN macrophages and CD3 T cells were abundantly present in RA synovia whereas T cells were scarce in OA or trauma synovial specimens.

During RA the synovium transforms from an organ focussed on maintaining local homeostasis to an organ that becomes a component of the systemic lymphoid system and eventually to a partially transformed, invasive and destructive chronic inflammatory tissue. The results presented herein indicate that in the RA synovium, metalloproteinase producing CD68 positive macrophages that express DC markers like DC-SIGN contribute to bone and cartilage destruction. The presence of ICAM-3 positive naive T cells in the immediate vicinity of these cells in RA, but not in OA and trauma patients, indicates that functional DC-SIGN/ICAM-3 interactions contribute to the development of disease.

Also provided herein is a diagnostic method for rheumatoid arthritis. Assaying the synovium of a patient for the presence of DC-SIGN expressing macrophage cells is used to make a diagnosis. The presence of greater than 50%, preferably greater than 60%, and most preferably greater than 70%, of the inflammatory cells being DC-SIGN positive is an indication that the person being tested has rheumatoid arthritis.

It is further seen that the knowledge that a large percentage of macrophage cells in the synovium of rheumatoid arthritis patients is used to purify such macrophage cells. Agents that bind DC-SIGN can be, for example, affixed to a solid support and a sample of cells can be contacted to said support and the support can then be washed to remove cells not bound by the agent. Such agents can include various carbohydrates, lectins, antibiotics, sugars and antibodies as discussed above that bind to DC-SIGN.

The following Examples are offered by way of illustration and are not intended to limit the disclosure in any manner. Standard techniques well known in the art or the techniques specifically described below are utilized.

EXAMPLE 1

Patients and Samples

Synovial samples were collected from 10 RA patients who were undergoing total joint replacement. For comparison, 10 synovial samples from osteoarthrosis and "trauma" patients were collected. Tissue specimens were embedded in Tissue-TekOCT (Miles Inc. Diagnostic Division, Elkhart, Ind.) and snap frozen in liquid nitrogen. Cryostat sections (7 μm) were mounted on superfrost slides and stored at −70° C. until further processing.

EXAMPLE 2

Antibodies

Monoclonal antibodies were purchased from various suppliers. Anti-CD68 (EBM 11, mature macrophages; MRP8/14, activated macrophages; Dako, Glostrup, Denmark), anti-CD14 (TUK4, monocytes; Dako, Glostrup Denmark), anti-CD3 (UCHT1, T cells; Dako, Glostrup, Denmark), anti-CD45RO (memory T cells; Dako, Glostrup, Denmark), anti-CD45RA (resting T cells; Dako, Glostrup, Denmark); anti-CD83 (mature DC), anti-DC-LAMP (mature DC), and Fascin (mature DC) from Immunotech, Marseille, France; anti-MMP-1 (R&D, USA) and anti-EMPRINN (Chemicon International Inc., USA). Anti-DC-SIGN mAb AZN-D1 and AZN-D2 were obtained by screening hybridoma supernatants of human DC-immunized BALB/c mice for the ability to block adhesion of DC to ICAM-3, as measured by the fluorescent bead adhesion assay (Geijtenbeek et al., 2000).

EXAMPLE 3

Immunohistochemical Analysis

Serial sections of synovia were stained for several markers. For each marker, all sections were stained in the same run to minimize interassay variations. Cryostat sections were fixed in 100% cold acetone (10 minutes), washed with PBS and incubated with the first antibody (10 μg/mL) for 60 minutes at 37° C. Subsequently, sections were preincubated with normal horse serum to block a specific binding and with biotinylated horse anti-murine IgG. Slides were developed with ABC kit (Elite kit, Vector, Burlingame, Calif.), developed with diaminobenzidine (DAB) and counterstained with hematoxylin for 3 minutes. Controls consisted of a) irrelevant primary isotype specific IgG1 and IgG2a antibodies (DAKO) and b) by omitting secondary antibodies.

For double-labeling experiments, the two antigens of interest were immunolabeled sequentially or simultaneously. Labeling of the first antibody used in the protocol for single-label immunohistochemistry described above. Following the first reaction using DAB chromagen (0.07% 3',3-diaminobenzadine), sections were rinsed in TBS (Tris buffered saline: 20 mM Tris, 150 mM NaCl, 2 mM $MgCl_2$, 1 mM $CaCl_2$), replaced in blocking solution (TBS containing 10% human serum) for 2 hours and then incubated with a secondary biotinylated anti-DC-SIGN for 2 hours. Subsequently, sections were incubated in ABC (Vector Labs) kit for 2 hours at room temperature. After further rinsing (TBS followed by 20 mM Tris buffer, pH 7.6) sections were reacted for a second time using Fast-blue as a chromagen, which yields a blue reaction product that is clearly distinguishable from the brown DAB label. Furthermore, double staining was performed using goat anti-mouse antibodies either coupled to Alexa 568 or Alexa 647 (Molecular Probes, The Netherlands). The latter synovia were visualized in the confocal microscope.

EXAMPLE 4

Scoring of Synovial Cells

Sections were labeled in a random way to allow blind scoring of the sections. Two observers using a semiquantitative five point scale (from 0 to 4) scored positive stained cells in each section. Differences of 1 point in readings were averaged, while differences exceeding one point were resolved by mutual agreement.

EXAMPLE 5

Reverse Transcriptase-Polymerase Chain Reaction (RT-PCR) and Sequencing

Five RA and OA synovial samples were analyzed for the presence of DC-SIGN messenger RNA (mRNA) levels. mRNA derived from monocytes treated with GM-CSF and IL-4 was used as control. Extraction was performed using the TRIZOL method. From each sample 60 nanograms of mRNA was used for the first strand complementary DNA (cDNA) synthesis, which was performed using oligo(dT)12-18 for priming and RNAse for removal of mRNA according to the manufacturer's protocol (QIAGEN, Chatsworth, Calif.).

PCR amplification was performed using 0.2 µM of target-specific primers (for DC-SIGN, sense 5'-AGAGTGGGGT-GACATGAGTG-3' (SEQ ID NO:3) and antisense 5'-GAAGTTCTGCTACGCAGGAG-3' (SEQ ID NO:4) producing a 1237 bp band; and for GAPDH (glyceraldehyde phosphate dehydrogenase), sense 5'-AACTCCCTCAAGAT-TGTCAG CA-3' (SEQ ID NO:5) and antisense 5'-TCCAC-CACCCTGTTGCTGTA-3' (SEQ ID NO:6) producing a 553 bp product), 100 µM of dATP, dCTP, dGTP and dTTP, and two units of the thermostable DNA polymerase (Invitrogen) in 50 µl of PCR buffer (10 mM Tris HCl, pH 8.8, 1.5 mM MgCl$_2$, 50 mM KCl, 0.1% Triton X-100).

For the DC-SIGN primers, the corresponding sequence was searched from the NCBI (National Center for Biotechnology Information) Entrez system. Primers for DC-SIGN and GAPDH were purchased from Eurogentec (Belgium).

The reaction was run in a thermal cycler (Peltier Thermal Cycler, MJ Research, Biozym) for 35 cycles of 1 minute of denaturation at 95° C., 1 minute of annealing at 60° C. and 1 minute of extension at 72° C.

Amplified DNA was run on a 1% agarose gel (Gibco BRL) and visualized with ethidium bromide for size verification. PCR fragments from one RA patient and a positive monocyte control sample were extracted from the gel using silica-gel membrane-based QIAquick columns (QIAGEN, Chatsworth, Calif.) and quantified photospectrometrically. Approximately 50 ng of DNA fragments was sequenced using fluorescein-labeled dye terminator kits and analyzed on Applied Biosystems automatic sequencer model. The acquired sequence was verified with the NCBI BLASTN program.

EXAMPLE 6

FACS Analysis

EDTA blood was isolated from five RA patients and five controls. One hundred µL of total blood was incubated with 100 µL of the first antibody solution (100 µg/mL) and incubated during 30 minutes. Anti-DC-SIGN, anti-CD14 and isotype specific control monoclonal antibodies were used. After washing with immunofluorescence buffer (PBS+1% BSA, pH 7.4), cells were centrifuged for 5 minutes at 1500 rpm and the fluorescent conjugate (goat anti-mouse F(ab')$_2$ labeled with FITC) was added. After 30 minutes incubation at 4° C., cells were washed and the pellet was resuspended in 500 µL immunofluorescence buffer. Omitting the first antibody and substitution of anti-DC-SIGN and anti-CD14 for isotype matched irrelevant antibodies (DAKO, Glostrup, Denmark) was used as a negative control. FACS-analysis was performed using a Coulter Epics XL/XL-MCL (Coulter Electronics Ltd., Mijdrecht, The Netherlands). The window was set in such a way that >95% of cells were CD14 positive, indicating that >95% of cells were monocytes.

It will be appreciated that the methods and compositions described above can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Barrera P, et al. (2000). *Arthritis Rheum.* 43:1951-1959.
Bresnihan B, et al. (1998). *Arthritis Rheum.* 41:2196-2204.
Cameron P U, et al. (1992). *Science* 257:383-387.
Cawston T (1998). *Mol. Med. Today* 4:130-137.
Chizzolini C, et al. (2000). *J. Immunol.* 164:5952-5960.
Curtis B M, et al. (1992). *Proc. Natl. Acad. Sci. USA* 89:8356-8360.
Dayer J M and Burger D (1994). *Eur. Cytokine Netw.* 5:563-571.
el-Gabalawy H, et al. (1994). *Arthritis Rheum.* 37:846-854.
Feldmann M, et al. (1996). *Annu. Rev. Immunol.* 14:397-440.
Firestein G S and Zvaifler N J (1990). *Arthritis Rheum.* 33:768-773.
Firestein G S and Zvaifler N J (2002). *Arthritis Rheum.* 46:298-308.
Fox D A (1997). *Arthritis Rheum.* 40:598-609.
Fox D A, et al. (1990). *J. Clin. Invest.* 86:1124-1136.
Geijtenbeek T B H, et al. (2000). *Cell* 100:575-585.
Hosaka S, et al. (1996). *Clin. Immunol. Immunopathol.* 78:276-282.
Huse W D, et al. (1989). *Science* 246:1275-1281.
Janeway-Travers: "*Immunobiology, the immune system in health and disease*", Third Edition.
Jonuleit H, et al. (1996). *Arch. Dermatol. Res.* 289:1-8.
Katrib A, et al. (2001). *Rheumatology* 40:988-994.
Kerr J F, et al. (1972). *Br. J. Cancer* 26: 239-257.
Kinne R W, et al. (2000). *Arthritis Res.* 2:189-202.
Klippel J H (Ed): "*Primer on the Rheumatic Diseases*" Atlanta, Ga., Arthritis Foundation, 1997.
Mitchell D (1985). *Rheumatoid Arthritis*. P D Utsinger, N J Zvaifler, G E Ehrlich, eds. J.B. Lippincott Co., Philadelphia, pp. 133-150.
Mulherin D, et al. (1996). *Arthritis Rheum.* 39:115-124.
Nassonov E L, et al. (2000). *Rheumatology* 39:808-810.

Panayi G S (1999). *Rheumatology* 38 (Suppl2):8-10.
Pap T, et al. (2000). *Arthritis Res.* 2:361-367.
Roitt I, et al. (1994). *"Immunology"*, 2nd Ed., Churchill Livingstone.
Schulze-Koops H and Lipsky P E (2000). *Curr. Dir. Autoimmun.* 2:24-49.
Sites D P, et al. (1994). *"Basic and clinical immunology"*, 8th Ed., Prentice-Hall.
Steinman R M (2000). *Cell* 100:491-494.
Summers K L, et al. (1994). *Clin. Exp. Immunol.* 97:39-44.
Szekanecz Z, et al. (1994). *Arthritis Rheum.* 37:221-231.
Tomita T, et al. (2002). *Arthritis Rheum.* 46:373-378.
van den Berg W B and van Lent P L (1996). *Immunobiology* 195:614-623.
Vazeux R, et al. (1992). *Nature* 360:485-488.
Wernicke D, et al. (2002). *Arthritis Rheum.* 46:64-74.
Wyllie A H, et al. (1980). *Int. Rev. Cytol.* 68: 251-306.
Yanni G, et al. (1994). *Ann. Rheum. Dis.* 53:39-44.
WO 93/01820
WO 95/32734
WO 96/23882
WO 98/02456
WO 98/41633
WO 98/49306
WO 00/63251

The invention claimed is:

1. A method for enriching the percentage of macrophages in a synovial sample of cells, the method comprising:
   contacting a sample of cells with an antibody that binds to a protein having the amino acid sequence of SEQ ID NO:2 (DC-SIGN), or an antigen-binding fragment of said antibody, wherein said sample of cells is obtained from a person with rheumatoid arthritis; and
   separating cells that bind to said antibody or antigen binding fragment from cells that do not bind to said antibody or antigen binding fragment to thereby enrich the percentage of macrophages in said sample of cells.

2. The method of claim 1 wherein said antibody is (i) an antibody produced by hybridoma ECACC accession number 99040818, or (ii) an antibody produced by hybridoma ECACC accession number 99040819.

3. The method of claim 1 wherein said antibody or antigen binding fragment is attached to a solid support.

4. The method of claim 1 wherein said sample is a synovial fluid sample.

5. The method of claim 1 wherein said sample is a synovial membrane sample.

6. The method of claim 1 wherein said separating comprises flow-cytometry or FACS.

7. The method of claim 1 further comprising contacting said sample of cells with an antibody that binds to CD68, or an antigen-binding fragment thereof.

* * * * *

SEQUENCE LISTING

```
<160> NUMBER OF SEQ ID NOS: 6

<210> SEQ ID NO 1
<211> LENGTH: 1215
<212> TYPE: DNA
<213> ORGANISM: Homo sapiens
<220> FEATURE:
<221> NAME/KEY: CDS
<222> LOCATION: (1)..(1212)

<400> SEQUENCE: 1 atg agt gac tcc aag gaa cca aga ctg cag cag ctg ggc ctc ctg gag      48
Met Ser Asp Ser Lys Glu Pro Arg Leu Gln Gln Leu Gly Leu Leu Glu
1               5                   10                  15 gag gaa cag ctg aga ggc ctt gga ttc cga cag act cga gga tac aag      96
Glu Glu Gln Leu Arg Gly Leu Gly Phe Arg Gln Thr Arg Gly Tyr Lys
            20                  25                  30 agc tta gca ggg tgt ctt ggc cat ggt ccc ctg gtg ctg caa ctc ctc     144
Ser Leu Ala Gly Cys Leu Gly His Gly Pro Leu Val Leu Gln Leu Leu
        35                  40                  45 tcc ttc acg ctc ttg gct ggg ctc ctt gtc caa gtg tcc aag gtc ccc     192
Ser Phe Thr Leu Leu Ala Gly Leu Leu Val Gln Val Ser Lys Val Pro
    50                  55                  60 agc tcc ata agt cag gaa caa tcc agg caa gac gcg atc tac cag aac     240
Ser Ser Ile Ser Gln Glu Gln Ser Arg Gln Asp Ala Ile Tyr Gln Asn
65                  70                  75                  80 ctg acc cag ctt aaa gct gca gtg ggt gag ctc tca gag aaa tcc aag     288
Leu Thr Gln Leu Lys Ala Ala Val Gly Glu Leu Ser Glu Lys Ser Lys
                85                  90                  95 ctg cag gag atc tac cag gag ctg acc cag ctg aag gct gca gtg ggt     336
Leu Gln Glu Ile Tyr Gln Glu Leu Thr Gln Leu Lys Ala Ala Val Gly
            100                 105                 110 gag ctt cca gag aaa tct aag ctg cag gag atc tac cag gag ctg acc     384
Glu Leu Pro Glu Lys Ser Lys Leu Gln Glu Ile Tyr Gln Glu Leu Thr
        115                 120                 125 cgg ctg aag gct gca gtg ggt gag ctt cca gag aaa tct aag ctg cag     432
Arg Leu Lys Ala Ala Val Gly Glu Leu Pro Glu Lys Ser Lys Leu Gln
    130                 135                 140 gag atc tac cag gag ctg acc tgg ctg aag gct gca gtg ggt gag ctt     480
Glu Ile Tyr Gln Glu Leu Thr Trp Leu Lys Ala Ala Val Gly Glu Leu
145                 150                 155                 160 cca gag aaa tct aag atg cag gag atc tac cag gag ctg act cgg ctg     528
Pro Glu Lys Ser Lys Met Gln Glu Ile Tyr Gln Glu Leu Thr Arg Leu
                165                 170                 175 aag gct gca gtg ggt gag ctt cca gag aaa tct aag cag cag gag atc     576
Lys Ala Ala Val Gly Glu Leu Pro Glu Lys Ser Lys Gln Gln Glu Ile
            180                 185                 190
```

```
tac cag gag ctg acc cgg ctg aag gct gca gtg ggt gag ctt cca gag      624
Tyr Gln Glu Leu Thr Arg Leu Lys Ala Ala Val Gly Glu Leu Pro Glu
                195                 200                 205 aaa tct aag cag cag gag atc tac cag gag ctg acc cgg ctg aag gct      672
Lys Ser Lys Gln Gln Glu Ile Tyr Gln Glu Leu Thr Arg Leu Lys Ala
    210                 215                 220 gca gtg ggt gag ctt cca gag aaa tct aag cag cag gag atc tac cag      720
Ala Val Gly Glu Leu Pro Glu Lys Ser Lys Gln Gln Glu Ile Tyr Gln
225                 230                 235                 240 gag ctg acc cag ctg aag gct gca gtg gaa cgc ctg tgc cac ccc tgt      768
Glu Leu Thr Gln Leu Lys Ala Ala Val Glu Arg Leu Cys His Pro Cys
                245                 250                 255 ccc tgg gaa tgg aca ttc ttc caa gga aac tgt tac ttc atg tct aac      816
Pro Trp Glu Trp Thr Phe Phe Gln Gly Asn Cys Tyr Phe Met Ser Asn
                260                 265                 270 tcc cag cgg aac tgg cac gac tcc atc acc gcc tgc aaa gaa gtg ggg      864
Ser Gln Arg Asn Trp His Asp Ser Ile Thr Ala Cys Lys Glu Val Gly
        275                 280                 285 gcc cag ctc gtc gta atc aaa agt gct gag gag cag aac ttc cta cag      912
Ala Gln Leu Val Val Ile Lys Ser Ala Glu Glu Gln Asn Phe Leu Gln
    290                 295                 300 ctg cag tct tcc aga agt aac cgc ttc acc tgg atg gga ctt tca gat      960
Leu Gln Ser Ser Arg Ser Asn Arg Phe Thr Trp Met Gly Leu Ser Asp
305                 310                 315                 320 cta aat cag gaa ggc acg tgg caa tgg gtg gac ggc tca cct ctg ttg     1008
Leu Asn Gln Glu Gly Thr Trp Gln Trp Val Asp Gly Ser Pro Leu Leu
                325                 330                 335 ccc agc ttc aag cag tat tgg aac aga gga gag ccc aac aac gtt ggg     1056
Pro Ser Phe Lys Gln Tyr Trp Asn Arg Gly Glu Pro Asn Asn Val Gly
                340                 345                 350 gag gaa gac tgc gcg gaa ttt agt ggc aat ggc tgg aac gac gac aaa     1104
Glu Glu Asp Cys Ala Glu Phe Ser Gly Asn Gly Trp Asn Asp Asp Lys
        355                 360                 365 tgt aat ctt gcc aaa ttc tgg atc tgc aaa aag tcc gca gcc tcc tgc     1152
Cys Asn Leu Ala Lys Phe Trp Ile Cys Lys Lys Ser Ala Ala Ser Cys
    370                 375                 380 tcc agg gat gaa gaa cag ttt ctt tct cca gcc cct gcc acc cca aac     1200
Ser Arg Asp Glu Glu Gln Phe Leu Ser Pro Ala Pro Ala Thr Pro Asn
385                 390                 395                 400 ccc cct cct gcg tag                                                  1215
Pro Pro Pro Ala <210> SEQ ID NO 2
<211> LENGTH: 404
<212> TYPE: PRT
<213> ORGANISM: Homo sapiens

<400> SEQUENCE: 2

Met Ser Asp Ser Lys Glu Pro Arg Leu Gln Gln Leu Gly Leu Leu Glu
1               5                   10                  15

Glu Glu Gln Leu Arg Gly Leu Gly Phe Arg Gln Thr Arg Gly Tyr Lys
                20                  25                  30

Ser Leu Ala Gly Cys Leu Gly His Gly Pro Leu Val Leu Gln Leu Leu
            35                  40                  45

Ser Phe Thr Leu Leu Ala Gly Leu Leu Val Gln Val Ser Lys Val Pro
        50                  55                  60

Ser Ser Ile Ser Gln Glu Gln Ser Arg Gln Asp Ala Ile Tyr Gln Asn
65                  70                  75                  80
```

```
Leu Thr Gln Leu Lys Ala Ala Val Gly Glu Leu Ser Glu Lys Ser Lys
                85                  90                  95

Leu Gln Glu Ile Tyr Gln Glu Leu Thr Gln Leu Lys Ala Ala Val Gly
            100                 105                 110

Glu Leu Pro Glu Lys Ser Lys Leu Gln Glu Ile Tyr Gln Glu Leu Thr
        115                 120                 125

Arg Leu Lys Ala Ala Val Gly Glu Leu Pro Glu Lys Ser Lys Leu Gln
    130                 135                 140

Glu Ile Tyr Gln Glu Leu Thr Trp Leu Lys Ala Ala Val Gly Glu Leu
145                 150                 155                 160

Pro Glu Lys Ser Lys Met Gln Glu Ile Tyr Gln Glu Leu Thr Arg Leu
                165                 170                 175

Lys Ala Ala Val Gly Glu Leu Pro Glu Lys Ser Lys Gln Gln Glu Ile
            180                 185                 190

Tyr Gln Glu Leu Thr Arg Leu Lys Ala Ala Val Gly Glu Leu Pro Glu
        195                 200                 205

Lys Ser Lys Gln Gln Glu Ile Tyr Gln Glu Leu Thr Arg Leu Lys Ala
    210                 215                 220

Ala Val Gly Glu Leu Pro Glu Lys Ser Lys Gln Gln Glu Ile Tyr Gln
225                 230                 235                 240

Glu Leu Thr Gln Leu Lys Ala Ala Val Glu Arg Leu Cys His Pro Cys
                245                 250                 255

Pro Trp Glu Trp Thr Phe Phe Gln Gly Asn Cys Tyr Phe Met Ser Asn
            260                 265                 270

Ser Gln Arg Asn Trp His Asp Ser Ile Thr Ala Cys Lys Glu Val Gly
        275                 280                 285

Ala Gln Leu Val Val Ile Lys Ser Ala Glu Glu Gln Asn Phe Leu Gln
    290                 295                 300

Leu Gln Ser Ser Arg Ser Asn Arg Phe Thr Trp Met Gly Leu Ser Asp
305                 310                 315                 320

Leu Asn Gln Glu Gly Thr Trp Gln Trp Val Asp Gly Ser Pro Leu Leu
                325                 330                 335

Pro Ser Phe Lys Gln Tyr Trp Asn Arg Gly Glu Pro Asn Asn Val Gly
            340                 345                 350

Glu Glu Asp Cys Ala Glu Phe Ser Gly Asn Gly Trp Asn Asp Asp Lys
        355                 360                 365

Cys Asn Leu Ala Lys Phe Trp Ile Cys Lys Lys Ser Ala Ala Ser Cys
    370                 375                 380

Ser Arg Asp Glu Glu Gln Phe Leu Ser Pro Ala Pro Ala Thr Pro Asn
385                 390                 395                 400

Pro Pro Pro Ala
```

<210> SEQ ID NO 3
<211> LENGTH: 20
<212> TYPE: DNA
<213> ORGANISM: Artificial
<220> FEATURE:
<223> OTHER INFORMATION: Sense primer for PCR amplification of DC-SIGN

<400> SEQUENCE: 3
agagtggggt gacatgagtg         20

<210> SEQ ID NO 4
<211> LENGTH: 20
<212> TYPE: DNA
<213> ORGANISM: Artificial

```
-continued

<220> FEATURE:
<223> OTHER INFORMATION: Antisense primer for PCR amplification of
      DC-SIGN

<400> SEQUENCE: 4
gaagttctgc tacgcaggag                                                   20

<210> SEQ ID NO 5
<211> LENGTH: 22
<212> TYPE: DNA
<213> ORGANISM: Artificial
<220> FEATURE:
<223> OTHER INFORMATION: Sense primer for PCR amplification of GAPDH

<400> SEQUENCE: 5
aactccctca agattgtcag ca                                                22

<210> SEQ ID NO 6
<211> LENGTH: 20
<212> TYPE: DNA
<213> ORGANISM: Artificial
<220> FEATURE:
<223> OTHER INFORMATION: Antisense primer for PCR amplification of GAPDH

<400> SEQUENCE: 6
tccaccaccc tgttgctgta                                                   20
```